United States Patent
Drake et al.

(10) Patent No.: US 11,938,279 B2
(45) Date of Patent: Mar. 26, 2024

(54) VALVE CLAMP FOR DEVICE DELIVERY CATHETER HANDLE

(71) Applicant: Medtronic, Inc., Minneapolis, MN (US)

(72) Inventors: Ronald A. Drake, St. Louis Park, MN (US); Lester O. Stener, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 656 days.

(21) Appl. No.: 16/927,170

(22) Filed: Jul. 13, 2020

(65) Prior Publication Data
US 2021/0046281 A1 Feb. 18, 2021

Related U.S. Application Data

(60) Provisional application No. 62/887,144, filed on Aug. 15, 2019.

(51) Int. Cl.
*A61B 17/50* (2006.01)
*A61M 25/00* (2006.01)
(Continued)

(52) U.S. Cl.
CPC ......... *A61M 25/0082* (2013.01); *A61B 17/50* (2013.01); *A61M 25/0075* (2013.01);
(Continued)

(58) Field of Classification Search
CPC .......... A61M 25/0082; A61M 25/0075; A61M 25/0136; A61M 25/0147;
(Continued)

(56) References Cited

U.S. PATENT DOCUMENTS 4,326,520 A * 4/1982 Alley ................. A61M 25/0113
604/159
5,399,165 A * 3/1995 Paul, Jr. ............ A61M 25/0147
604/95.04
(Continued)

FOREIGN PATENT DOCUMENTS

WO 2008139852 A1 11/2008

OTHER PUBLICATIONS

International Search Report and Written Opinion of International Application No. PCT/US2020/045303, dated Nov. 26, 2020, 14 pp.
(Continued)

*Primary Examiner* — Kathleen S Holwerda
(74) *Attorney, Agent, or Firm* — Shumaker & Sieffert, P.A.

(57) ABSTRACT

In some examples, an implantable medical device delivery catheter comprises a handle and an elongated member disposed within the handle, the elongated member comprising an elongated member lumen configured to receive an inner tool that is configured to extend through a lumen of the delivery catheter, including the elongated member lumen, and interface with an implantable medical device. The handle further comprises a clamping assembly comprising a button configured to be actuated toward a longitudinal axis of the elongated member in a direction transverse to the longitudinal axis to compress the elongated member against the inner tool to restrain movement of the inner tool through the elongated member lumen.

23 Claims, 14 Drawing Sheets

(51) Int. Cl.
*A61M 25/01* (2006.01)
*A61N 1/36* (2006.01)
*A61N 1/362* (2006.01)

(52) U.S. Cl.
CPC .... *A61M 25/0136* (2013.01); *A61M 25/0147* (2013.01); *A61N 1/362* (2013.01)

(58) Field of Classification Search
CPC ........ A61M 2025/09125; A61M 39/06; A61M 39/0613; A61N 1/362; A61N 1/3756; A61B 17/3468; A61B 2017/347
USPC .................. 606/108, 129; 600/585; 604/250
See application file for complete search history.

(56) References Cited

U.S. PATENT DOCUMENTS

| | | | |
|---|---|---|---|
| 6,247,211 B1 | 6/2001 | Bell | |
| 6,551,284 B1 | 4/2003 | Greenberg et al. | |
| 2002/0095204 A1 | 7/2002 | Thompson et al. | |
| 2004/0172008 A1* | 9/2004 | Layer | A61M 39/0613 604/533 |
| 2007/0118079 A1* | 5/2007 | Moberg | A61M 25/0097 604/510 |
| 2007/0142784 A1 | 6/2007 | Dikeman et al. | |
| 2007/0219467 A1 | 9/2007 | Clark et al. | |
| 2007/0270755 A1* | 11/2007 | Von Oepen | B25B 9/00 600/585 |
| 2011/0077621 A1* | 3/2011 | Graham | A61M 39/1011 604/528 |
| 2014/0249540 A1* | 9/2014 | Nieman | A61B 17/221 606/113 |
| 2016/0015983 A1* | 1/2016 | Sheldon | A61B 17/3468 606/129 |
| 2016/0220829 A1 | 8/2016 | Wood | |
| 2017/0072180 A1* | 3/2017 | Balboni | A61M 25/0637 |
| 2018/0028805 A1 | 2/2018 | Anderson et al. | |
| 2018/0280703 A1 | 10/2018 | Hillukka et al. | |
| 2019/0201665 A1 | 7/2019 | Turpin | |

OTHER PUBLICATIONS

U.S. Appl. No. 16/847,315, filed Apr. 13, 2020, by Drake et al.
U.S. Appl. No. 16/596,252, filed Oct. 8, 2019, by Drake et al.

* cited by examiner

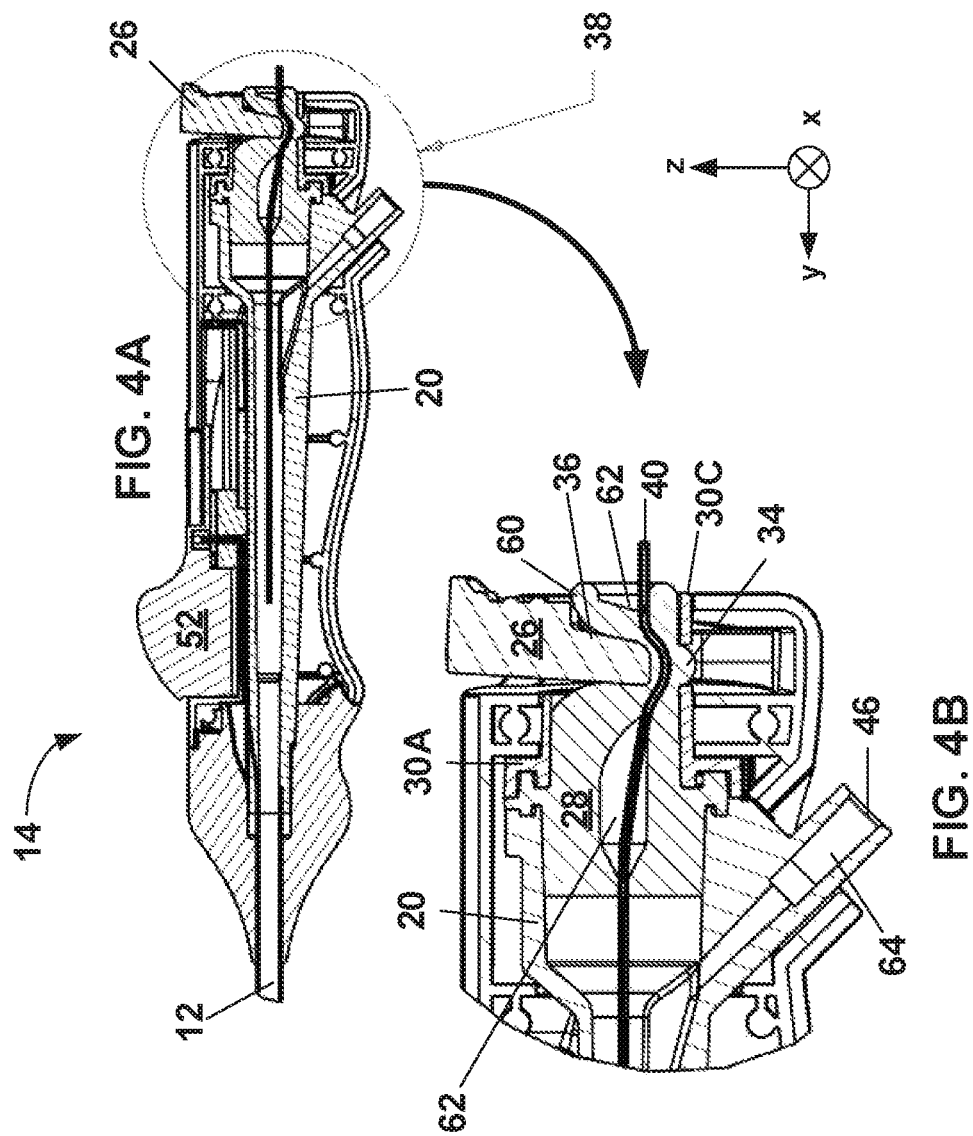

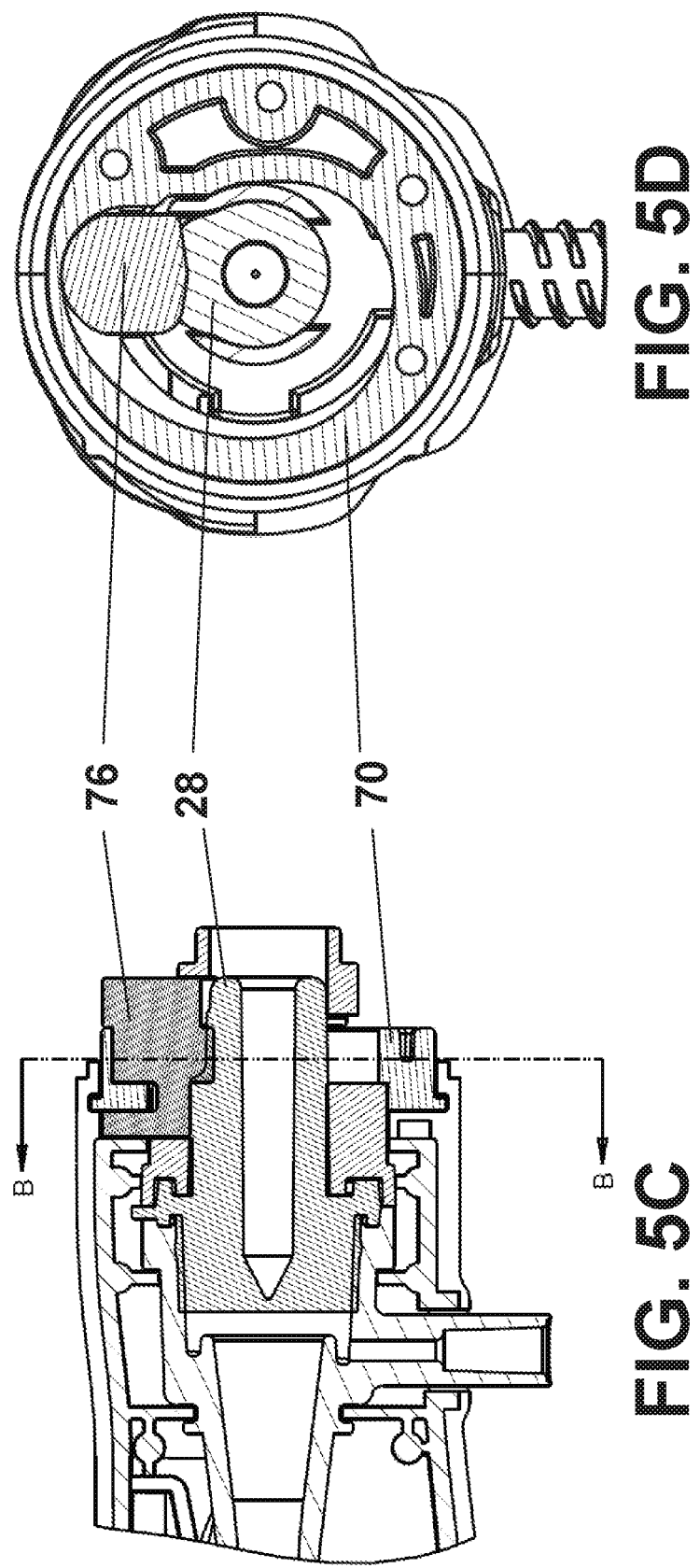

VALVE CLAMP FOR DEVICE DELIVERY CATHETER HANDLE

This application claims the benefit of U.S. Provisional Patent Application No. 62/887,144, filed Aug. 15, 2019, the entire content being incorporated herein by reference.

TECHNICAL FIELD

This disclosure relates generally to medical devices, and, more particularly, to systems for delivering medical devices.

BACKGROUND

Some types of implantable medical devices (IMDs), such as cardiac pacemakers or implantable cardiac defibrillator systems, may be used to provide cardiac sensing and therapy for a patient via one or more electrodes. Some IMDs include an implantable pulse generator that includes a housing that encloses electronic components, which may be configured to be implanted subcutaneously in the chest of the patient or within a chamber of a heart of the patient, as examples. IMDs having a pulse generator that is configured to be implanted within a chamber of the heart may be referred to as an intracardiac device or a leadless implantable medical device. A delivery catheter may be used to deliver an intracardiac device transvenously to an implant site within a heart of a patient and release the device after the device has been fixed at the implant site. The delivery catheter then may be withdrawn from the patient.

SUMMARY

In general, this disclosure is directed to delivery catheters and delivery systems for delivering an IMD within a vasculature of a patient. In some examples, a delivery system includes a delivery catheter that comprises a delivery catheter lumen, and an inner tool that may slidably extend through the delivery catheter lumen. The delivery catheter includes a handle, with an elongated member disposed within the handle. The elongated member defines an elongated member lumen, which is part of the delivery catheter lumen through which the inner tool may slidably extend. The handle also includes a clamping assembly configured to be actuated to selectively compress or pinch the elongated member against the inner tool in order to, for example, restrict movement of the inner tool through the elongated member lumen (and thereby through the delivery catheter lumen) or otherwise secure the inner tool in place within the delivery catheter lumen.

In one example, an implantable medical device delivery catheter comprises a shaft configured to extend through a vasculature of a patient, wherein the shaft comprises a shaft lumen extending from a proximal end of the shaft to a distal end of the shaft, and a handle connected to the proximal end of the shaft. The handle comprises an elongated member disposed within the handle, the elongated member comprising an elongated member lumen in fluid communication with the shaft lumen, wherein the elongated member lumen and the shaft lumen are configured to receive an inner tool configured to extend through the elongated member lumen and the shaft lumen and interface with the implantable medical device. The handle further comprises a clamping assembly comprising a button configured to be actuated toward a longitudinal axis of the elongated member in a direction transverse to the longitudinal axis to compress the elongated member against the inner tool to restrain movement of the inner tool through the elongated member lumen.

In another example, a method comprises engaging a clamping assembly of a handle of a medical device delivery catheter for a first time to restrain movement of an inner tool through an elongated member lumen of an elongated member disposed within the handle, wherein engaging the clamping assembly comprises actuating a button of the clamping assembly toward a longitudinal axis of the elongate member in a direction transverse to the longitudinal axis to compress the elongated member against the inner tool. The method further comprises, with the clamping assembly engaged for the first time, introducing a distal end of a shaft of the delivery catheter into a vasculature of a patient toward a tissue site, wherein the shaft comprises a shaft lumen extending from a proximal end of the shaft to a distal end of the shaft, wherein the handle is connected to the proximal end of the shaft, wherein the shaft lumen is in fluid communication with the elongated member lumen, wherein the shaft lumen and the elongated member lumen are configured to receive the inner tool, and wherein the inner tool is configured to interface with an implantable medical device. The method further comprises releasing the clamping assembly, wherein releasing the clamping assembly comprises actuating the button of the clamping assembly away from the longitudinal axis of the elongate member and, with the clamping assembly released, actuating the inner tool, wherein actuating the inner tool comprises moving the inner tool through the shaft lumen and the elongated member lumen. The method further comprises, after actuating the inner tool, engaging the clamping assembly a second time to restrain movement of the inner tool through the elongated member lumen and, with the clamping assembly engaged the second time, proximally withdrawing the shaft from the patient.

In another example, a system comprises an implantable medical device delivery catheter as described herein and an inner tool.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF THE DRAWINGS

FIGS. 4A and 4B are cross-sectional side views of the example delivery catheter of FIG. 1.

FIG. 5C is a longitudinal cross-sectional side view of a portion of the example delivery catheter of FIG. 5A.

FIG. 5D is a cross-sectional end view of a portion of the example delivery catheter of FIG. 5A, taken along line B-B in FIG. 5C.

DETAILED DESCRIPTION

Figure 1:
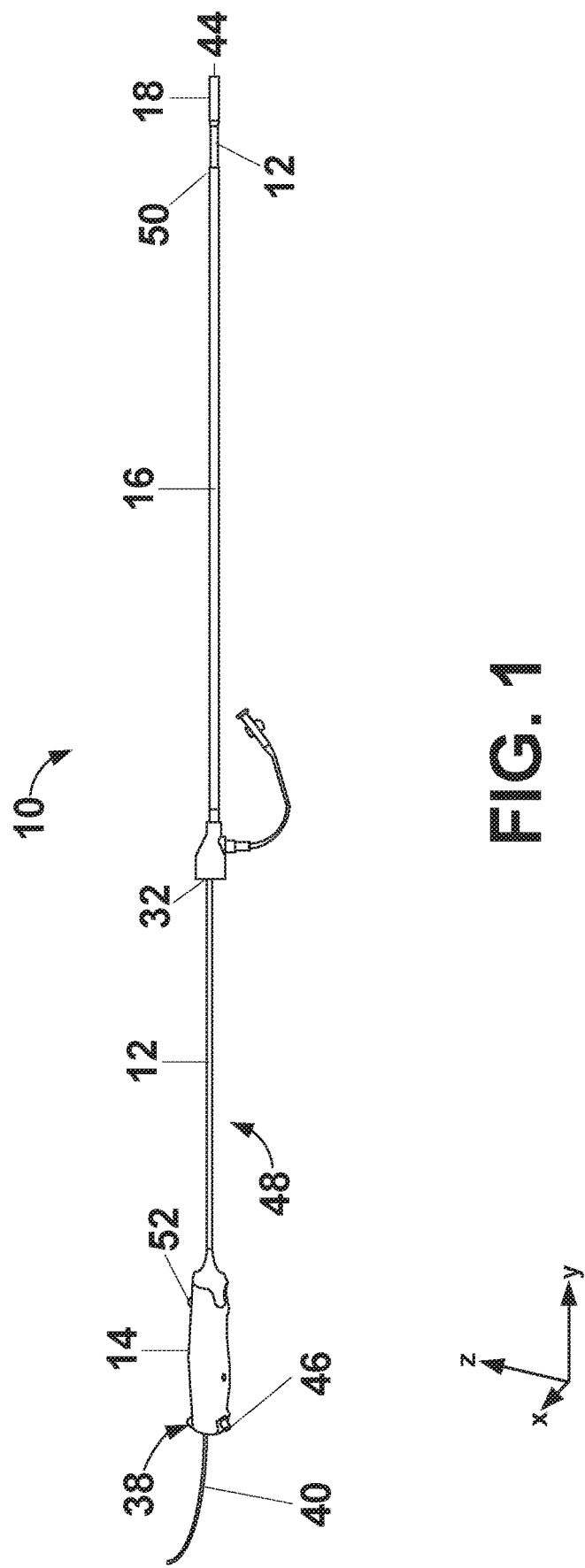
FIG. 1 is a side view illustrating a medical device delivery system, including an example delivery catheter, for delivering an implantable medical device (IMD) within a vasculature of patient.

In general, this disclosure describes devices and systems for introducing an implantable medical device (IMD) within a vasculature or other anatomy of a patient. FIG. 1 is a side view illustrating an example delivery system 10 for introducing an IMD, such as a pacemaker, within a vasculature or other anatomy of patient. System 10 includes inner member 48 and outer member 16. Although described herein in the context of delivering an IMD into the vasculature, e.g., heart, the devices, systems, and techniques of this disclosure may be used to deliver an IMD to any anatomical location.

Outer member 16 (also referred to as an "introducer") is an elongated tubular member defining an interior lumen. Outer member 16 includes proximal end 32 and distal end 50. Outer member 16 is configured to be inserted, such as by a physician, into a vasculature of a patient to provide a rigid channel (lumen) through which to insert a medical instrument, device, or other therapy.

Inner member 48 (also referred to as a "delivery catheter") is configured to be inserted through the lumen of outer member 16 to deliver a medical device within the vasculature. Inner member 48 includes elongated shaft 12, handle 14, and device cup 18. Handle 14 is connected to a proximal end of shaft 12, and may include one or more elements 52 configured to control the motion of the distal end of shaft 12. In some examples, handle 14 includes side port 46, for connection to a flushing assembly.

Device cup 18 is disposed at a distal end of shaft 12. Device cup 18 includes a hollow cylindrical body configured to house and support an IMD while the IMD is being implanted within a vasculature of a patient. For example, a physician may insert the distal end of inner member 48, including device cup 18, through the lumen of outer member 16, which is disposed within a vasculature of a patient. Once device cup 18 has extended through distal end 50 of outer member 16 and reached an implant site within the patient, the physician may release the IMD from distal opening 44 of device cup 18, for example, by actuating inner tool 40, e.g., moving inner tool 40 (e.g., a mechanical tether) through the shaft lumen 56 (FIG. 2A) of shaft 12 to advance the IMD through distal opening 44 and releasing the IMD from a distal end of inner tool 40. The physician may then withdraw shaft 12 and cup 18 proximally through outer member 16.

Inner tool 40 may slidably extend through a delivery catheter lumen (not shown in FIG. 1) of delivery catheter 48. It is to be understood that, although the present disclosure primarily describes examples in which inner tool 40 is a mechanical tether which is configured to release an IMD into a patient's anatomy, the disclosed techniques function similarly with respect to other inner tools configured to be advanced/retracted through a lumen defined by delivery catheter 48, such as a snare configured to retrieve an IMD from within a patient's anatomy. Hence, inner tool refers generally to a variety of mechanical components configured to interact with an IMD.

In some examples, delivery catheter lumen is defined by shaft lumen 56 (FIG. 2A) and one or more lumen of handle 14, such as a hub lumen 58 defined by a hub 20 (FIG. 3A) and valve lumen 62 defined by a valve 28 (FIGS. 3D-3F, 4B and 4C). Valve 28, or components thereof described herein, are examples of an elongated member within handle 14, and valve lumen 62, or the lumen of a component of the valve, are examples of an elongated member lumen configured to slidably receive inner tool 40. The handle lumen (e.g., including valve lumen 62 or another elongated member lumen) may be in fluid communication with shaft lumen 56 in order to define a continuous catheter lumen configured to slidably receive inner tool 40. In general, an elongated member may be a deformable (e.g., elastically deformable) structure defining a lumen, such as a tube, which may be formed from an elastically deformable material.

As will be described herein, handle 14 may include a clamping assembly 38 configured to be actuated to compress or pinch an elongated member within handle against inner tool 40 within the elongated member lumen, e.g., valve 28 and valve lumen 62. In this manner, the clamp may prevent or otherwise restrict longitudinal movement of inner tool 40 or another inner tool through the delivery catheter lumen. Features of clamping assembly 38 described herein may facilitate intuitive one-handed user actuation in a direction toward a longitudinal axis of the elongated member to engage the clamping assembly, locking the clamping assembly in the engaged position, and unlocking and disengaging the clamping assembly. In this manner, clamping assembly 38 may provide better control over the device delivery system, and in some examples, may enable the physician to implant or retrieve an IMD without requiring an assistant to operate either handle 14 or tool 40.

Figure 2A:
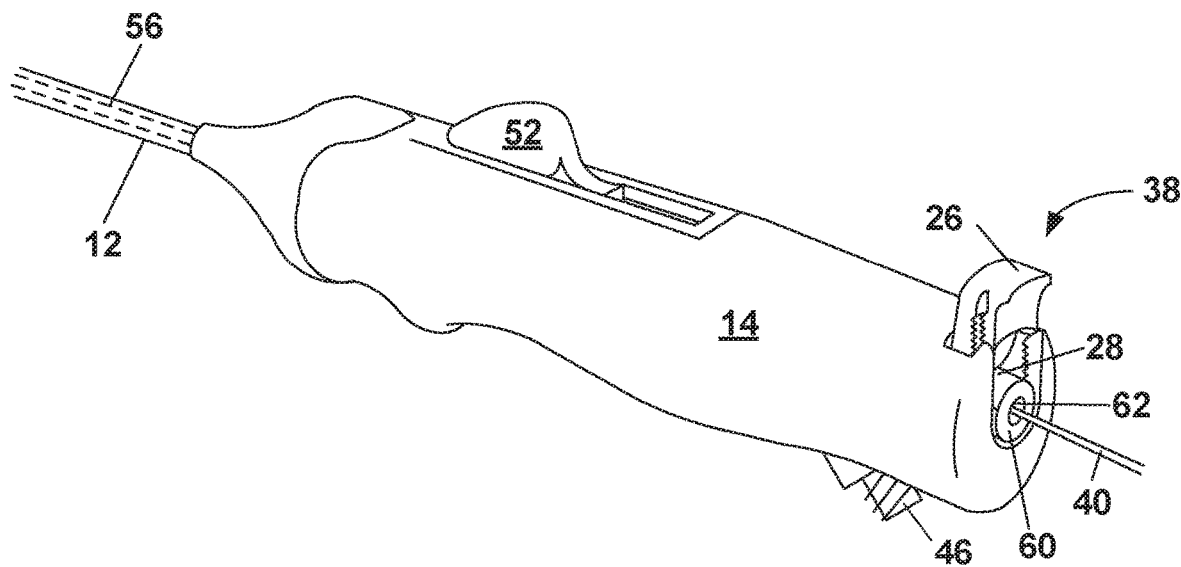
FIGS. 2A and 2B are perspective views of the proximal portion of the example delivery catheter of FIG. 1.
Figure 2B:
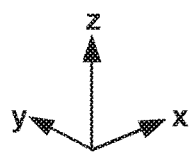
Figure 2B:
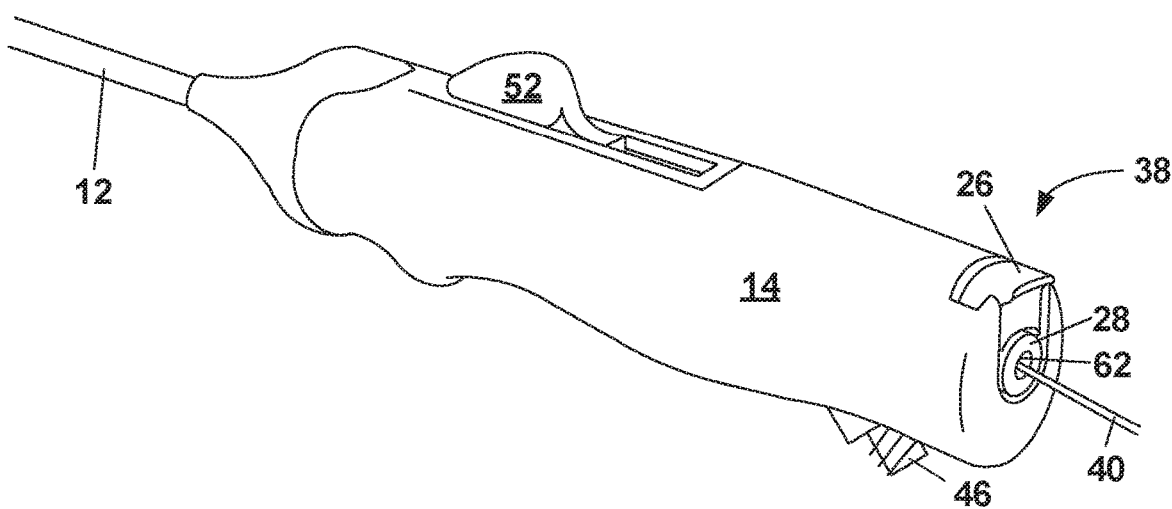

FIGS. 2A and 2B are perspective views of the proximal portion of delivery catheter 48, depicting handle 14 connected to a proximal end of shaft 12. FIGS. 2A and 2B include the x-y-z orthogonal coordinate system to serve as a frame of reference. In some examples in accordance with techniques of this disclosure, handle 14 includes a clamping assembly 38 configured to secure and retain inner tool 40 (such as a mechanical tether or snare) in place with respect to handle 14, e.g., to selectively prevent or allow movement of inner tool 40 through a lumen of delivery catheter 48 in the direction of the y-axis. In the illustrated example, clamping assembly 38 is located at a proximal end of handle 14, but may be located at other positions along handle 14 in other examples. Clamping assembly 38 may also create a redundant hemostatic seal for system 10. Clamping assembly 38 may be disposed in an "open" or unlocked position, as shown in FIG. 2A, or in a "closed" or locked position, as shown in FIG. 2B.

Clamping assembly 38 includes clamp button 26. Clamp button 26 is movable, e.g., in the negative-z-axis-direction, from the open position (FIG. 2A) to the closed position (FIG. 2B) in order to compress or pinch a valve 28 (e.g., a clamp tube 60 of valve 28) closed around inner tool 40. In other words, button 26 is configured to be actuated toward a central longitudinal axis of delivery catheter 48, e.g., of valve 28 and/or clamp tube 60, in a direction that is substantially transverse (normal) to the central longitudinal axis. The friction between valve 28 (for example, composed of a polymer such as rubber) and inner tool 40 when clamp button 26 is in the closed position and has deformed valve 28 may reduce or prevent any movement of inner tool 40 with respect to valve 28, such as proximally or distally along the y-axis direction. Clamp button 26 is also movable, e.g., in the positive-z-axis-direction, from the closed position (FIG. 2B) to the open position (FIG. 2A) to release inner tool 40. In other words, button 26 is configured to be actuated away from the central longitudinal axis of delivery catheter 48, in a direction that is substantially transverse (normal) to the central longitudinal axis. More specifically, as described further below, button 26 is configured to be actuated away from the central longitudinal axis of delivery catheter 48 in response to an applied pressure that is parallel with the central longitudinal axis in a direction of the distal end of delivery catheter 48. In this arrangement, the physician may easily actuate button 26 with the same hand holding handle 14, leaving his or her other hand free to hold the position of the shaft of delivery catheter 48 relative to the proximal end 32 of outer member 16 (thereby maintaining forward pressure on the delivery cup 18) without need for an assistant. Once button 26 is unlocked, that hand can then control tool 40.

Figure 3A:
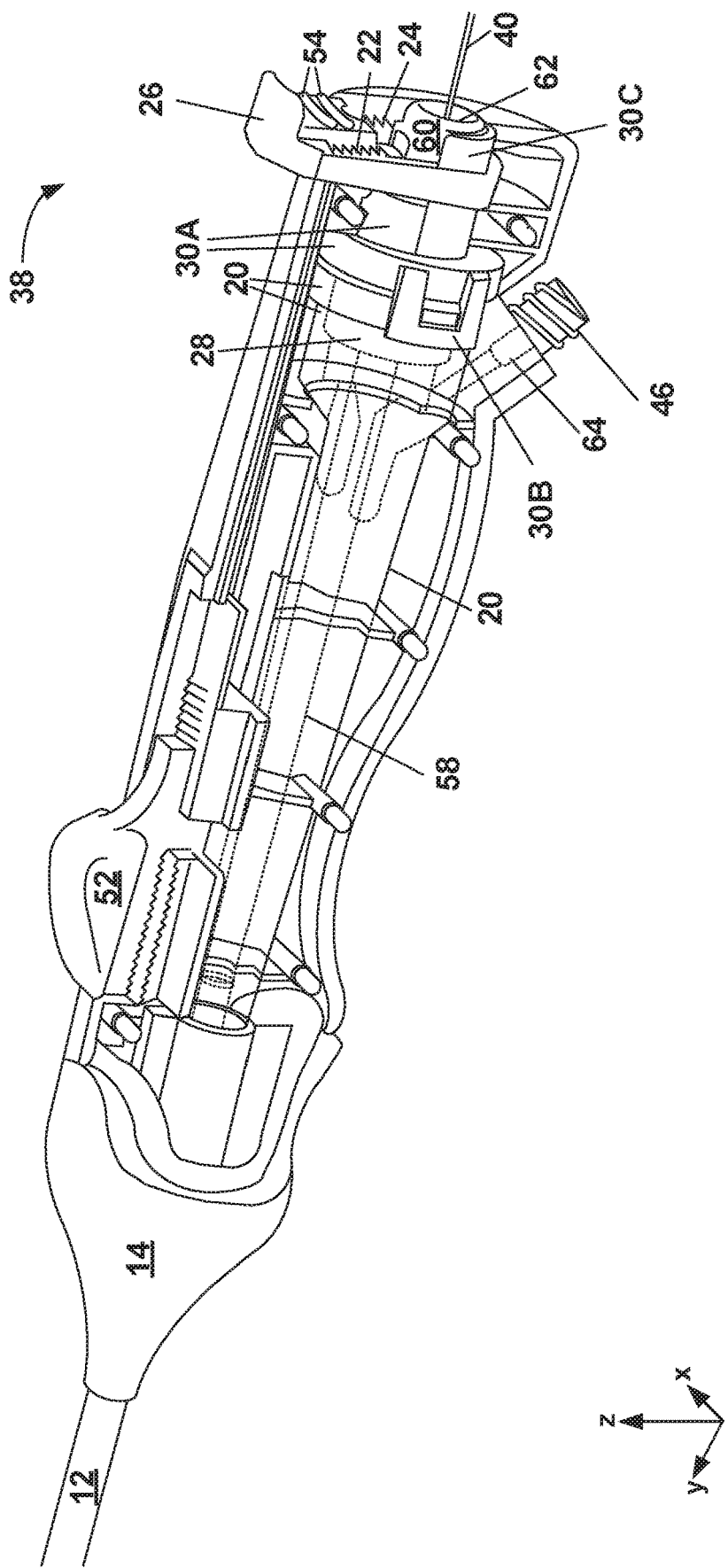
FIGS. 3A-3D are perspective views of the proximal portion of the example medical device delivery catheter of FIG. 1 with a portion of the outer housing removed.
Figure 3B:
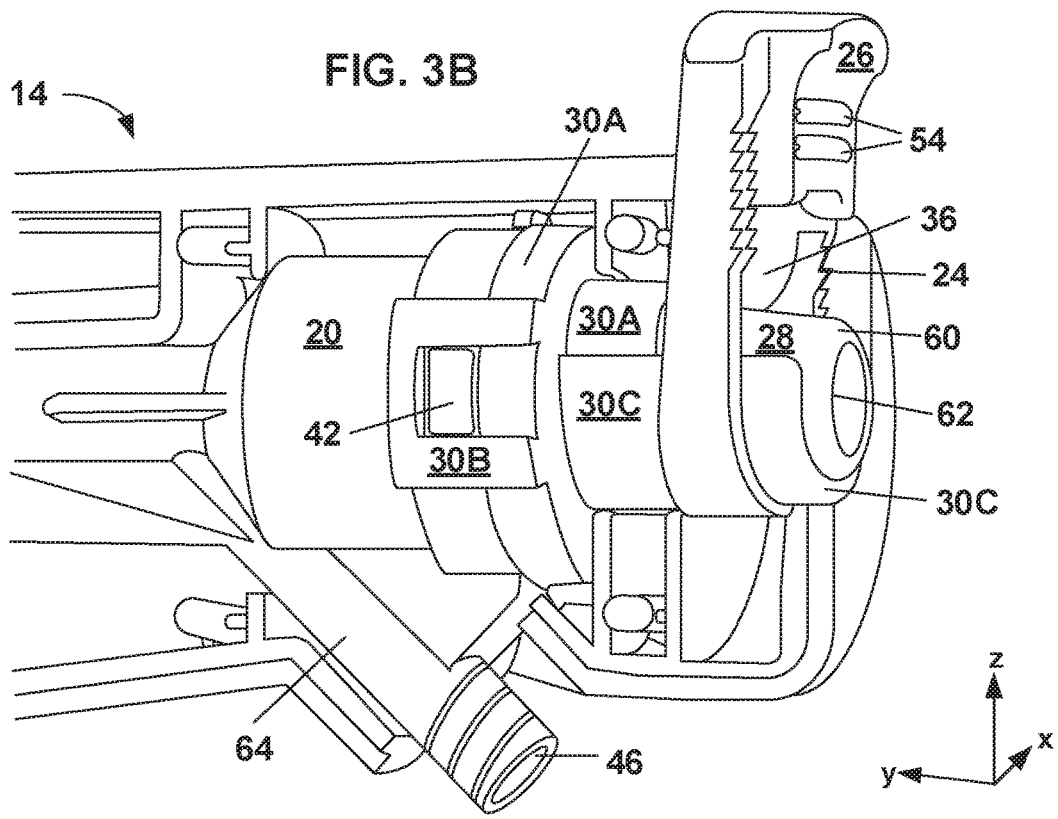
Figure 3C:
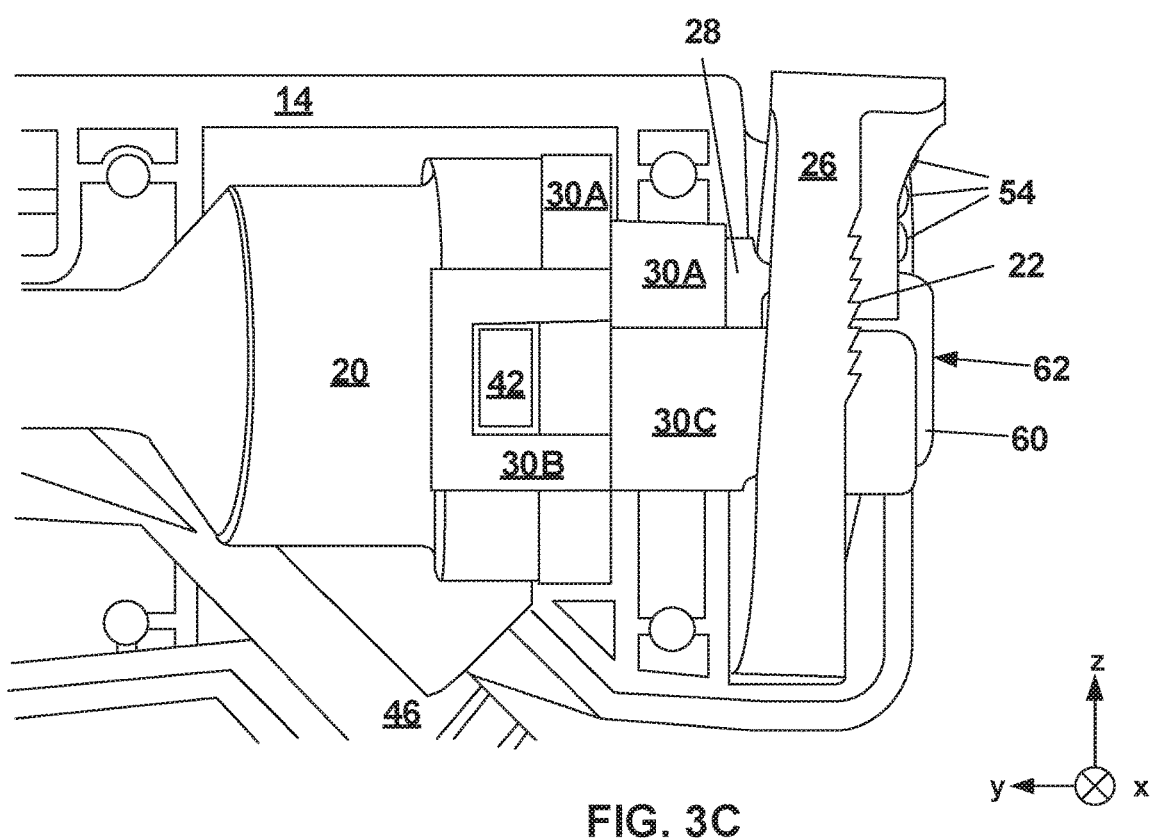
Figure 3D:
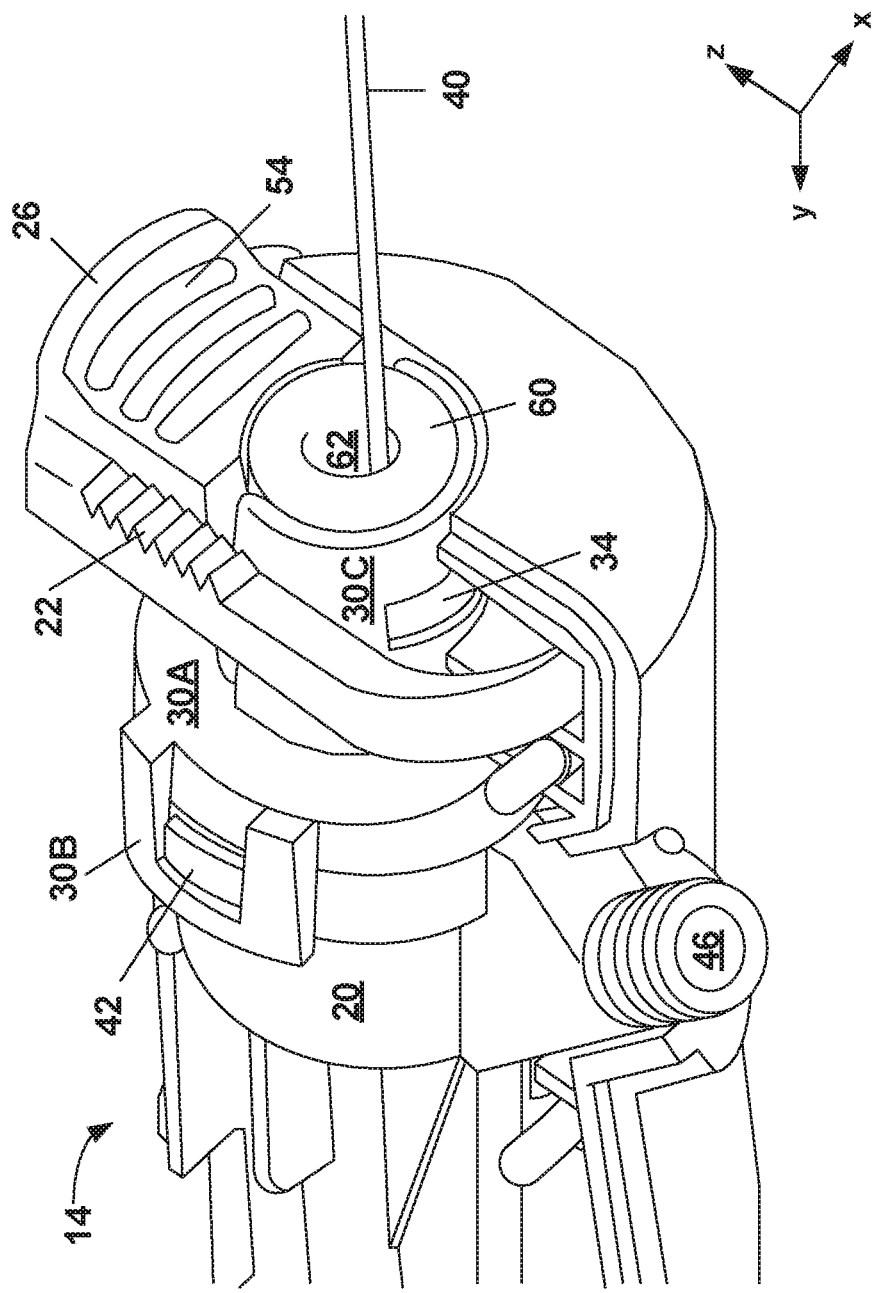

FIGS. 3A-3D are perspective views of the proximal portion of the medical device delivery catheter 48 of FIG. 1 with a portion of the outer housing removed to illustrate one or more interior components. Specifically, FIGS. 3A-3D illustrate handle 14 having clamping assembly 38. FIGS. 3A and 3B depict clamping assembly 38 in an "open", "unlocked", or "first" configuration. FIGS. 3C and 3D depict clamping assembly 38 in a "closed", "locked", or "second" configuration.

Clamping assembly 38 includes hub 20, valve cap portions 30A-30C (collectively referred to as "valve cap 30"), and button 26. In some examples, shaft 12 may extend proximally through handle 14 and connect to hub 20. Hub 20 may be a relatively rigid (e.g., plastic) material configured to connect shaft 12 to valve 28. In some examples, hub 20 may define a single inner hub lumen 58 extending through handle 14. In other examples, hub 20 may include a more complex shape, defining multiple branching lumens. For example, as illustrated by the example of FIG. 3A, hub 20 may define a secondary lumen 64 leading to side port 46 for connection to a flushing assembly.

Valve 28 is an elongated tubular member disposed inside a proximal portion of handle 14. Valve 28 (also referred to as "elongated member 28") defines an interior lumen (e.g., valve lumen 62 shown in FIGS. 4B and 4E, which may also be referred to as an elongated member lumen) in fluid communication with lumen 58 of hub 20. In some examples, valve 28 extends from the proximal end of handle 14 to shaft 12 at the distal end of handle 14. In other examples, valve 28 is disposed near the proximal end of handle 14, and is connected to another distinct elongated member, such as hub 20, extending the rest of the way through handle 14.

Valve 28 is composed of a relatively soft and/or springy material, e.g., an elastomeric material that tends to elastically return to its original shape or configuration after a compressive or distorting force has been removed. In some examples, valve 28 comprises a polymer, such as rubber.

Lumen 62 of valve 28 is configured to slidably receive, in at least some examples, an elongated inner tool 40. Inner tool 40 may comprise a string or cable-like element and be configured to attach, at its distal end, to an IMD located distal to the distal end of shaft 12, e.g., within or outside of the distal opening of delivery cup 18. Inner tool 40 may be configured to move proximally or distally through the lumen of valve 28. Inner tool 40 may include, for example, a mechanical tether configured to implant the IMD within a vasculature of a patient. In other examples, inner tool 40 may include a snare configured to retrieve the IMD from within the vasculature of the patient. In these examples, actuating inner tool 40 includes grabbing the IMD with a distal end of the snare.

The proximal end of valve 28 defines clamp tube 60, which may be an elongated member in some examples. Clamp tube 60 is an elongated extension of valve 28, configured in the manner described with respect to valve 28 to be compressed such that lumen 62 defined by valve 28 and clamp tube 60 pinches, or collapses around, inner tool 40, securing inner tool 40 in place via friction. Clamp tube 60 may partially extend out a proximal end of handle 14.

Valve cap 30 is a relatively rigid and/or durable (e.g., comprising a plastic) element configured to support and align the various other components of clamping mechanism 38. Valve cap 30 includes at least three sub-components 30A-30C, respectively, however, the three components may be molded or formed from a single unit, or from separate units and subsequently welded or otherwise joined together. Valve cap 30 is described further with respect to FIGS. 3E and 3F, below.

Clamp button 26 is an element formed from one or more relatively hard or durable materials (e.g., a plastic) configured to pinch and hold clamp tube 60 closed around inner tool 40. Clamp button 26 includes spade 36, proximal-facing teeth 22, and grips 54.

Spade 36 (shown in FIGS. 3B and 4A-4C) is a protrusion extending radially (e.g., in the negative-z-axis direction), or transverse to a longitudinal axis of handle 14, and toward clamp tube portion 60 of valve 28. Spade 36 is configured to contact and compress (or pinch) the outer surface of clamp tube portion 60 of valve 28. In some examples, spade 36 may be shaped similar to the head of a shovel, in that it is relatively thin along one axis (e.g., along the longitudinal axis of handle 14), so as to decrease the surface area of spade 36 contacting the outer surface of clamp tube 60, and accordingly, increase the pressure applied to clamp tube 60. For similar reasons, spade 36 may define a rounded tip configured to contact the outer surface of clamp tube 60. In other examples, spade 36 may define a substantially flat tip, which may be oriented perpendicular to the longitudinal axis of handle 14.

Clamp button 26 defines a pair of sets of proximal-facing teeth 22, one set disposed on either side (e.g., along the x-axis direction) of clamp button 26. Proximal-facing teeth are configured to secure clamp button 26 in the "locked" position, for example, by engaging with corresponding sets of distal-facing teeth 24 defined by the housing of handle 14. When placed in the "locked" position (FIGS. 3C and 3D), the soft (e.g., springy) composition of clamp tube 60 may press and hold proximal-facing teeth 22 proximally against distal-facing teeth 24, engaging the sets of teeth with one another.

In order to place clamping assembly 38 in the "locked" position shown in FIGS. 3C and 3D, a user may apply downward pressure (e.g., in the negative-z-axis direction) to the top of clamp button 26. This downward pressure will cause spade 36, extending from button 26, to depress downward into the material of clamp tube 60, elastically deforming the material of the tube and collapsing its inner lumen. In some examples, the outer surface of clamp tube 60 may define an inclined or ramp-like geometry, e.g., tapered or declining in a proximal direction. Accordingly, in response to the downward compressive force, the material of clamp tube 60 may elastically apply a restoring force against spade 36, in both proximal (negative-y-axis) and upward (z-axis) directions in such examples. The proximal and upward restoring force will press proximal-facing teeth 22 against distal-facing teeth 24, securing clamp button 26 in place, holding clamp tube 60 closed underneath spade 36, and securing mechanical tether 40 in place.

In order to release clamp button 26 back to the "unlocked" position (FIGS. 3A and 3B), the user may apply distal pressure (e.g., in the y-axis direction, toward the distal end of shaft 12) to clamp button 26, disengaging the two sets of teeth. In this manner, button 26 is configured to be actuated from the second "locked" position to the first "unlocked" position in response to a longitudinal force in a direction of the distal end of the catheter. The rubbery or springy composition of clamp tube 60 will tend to press clamp button 26 upward (e.g., in the z-axis direction), and back to the "unlocked" position. In some examples, the user may advantageously actuate the button between the locked and unlocked positions with one hand.

Figure 3E:
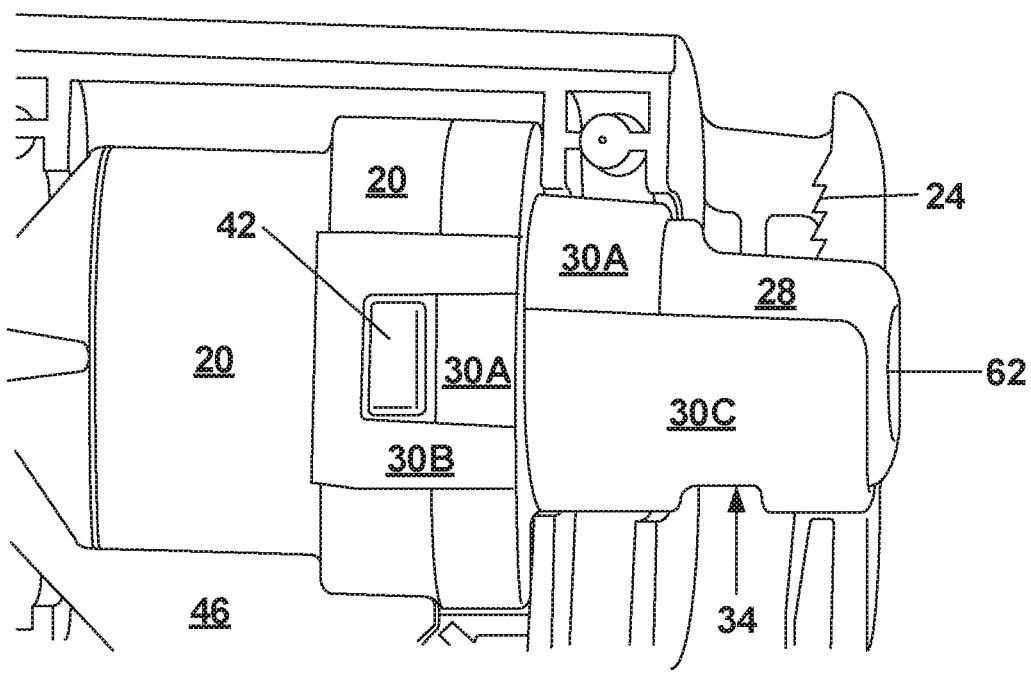
FIGS. 3E and 3F are perspective views of the proximal portion of the example medical device delivery catheter of FIG. 1 with a portion of the outer housing and the clamp button removed.
Figure 3F:
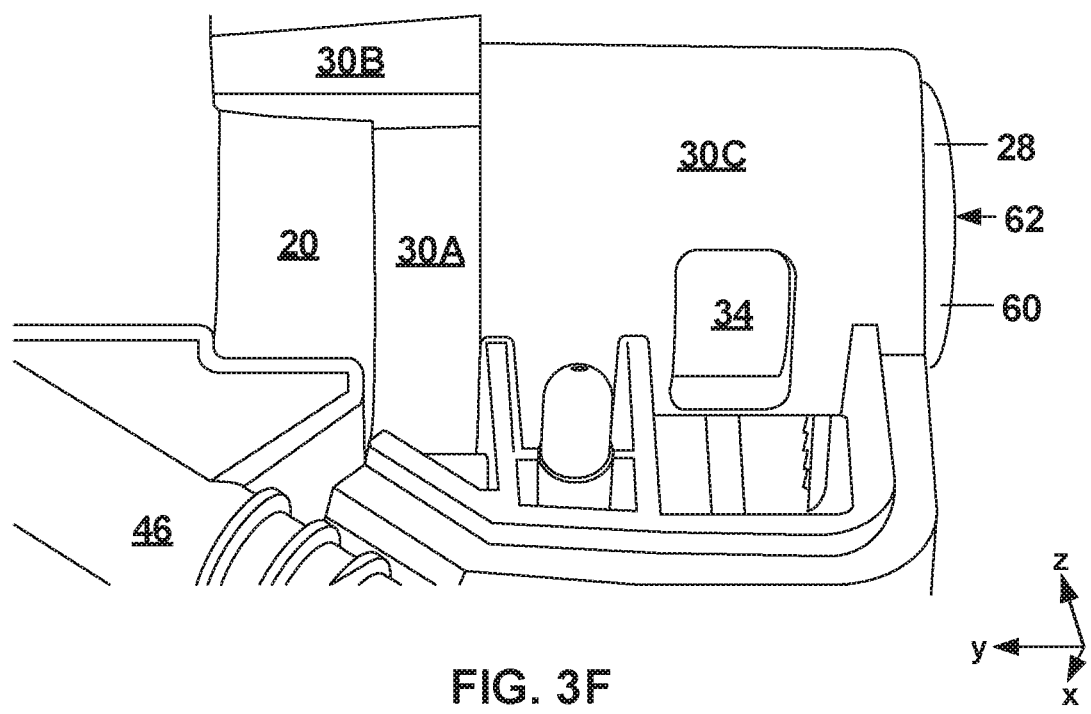

FIGS. 3E and 3F are perspective views of the proximal portion of the medical device delivery catheter of FIG. 1 with a portion of the housing, as well as the clamp button 26 removed, in order to illustrate one or more inner components. Specifically, FIGS. 3E and 3F illustrate valve cap components 30A-30C. Valve cap 30 is a relatively rigid or durable (e.g., composed of plastic) element configured to support and align the various other components of clamping mechanism 38 with respect to one another. During assembly, valve cap 30 fits over valve 28 and snaps onto hub 20. Valve cap 30 includes at least three structural components 30A-30C, respectively, however, the three components may be molded or formed from a single unit, or from separate units and subsequently welded or otherwise joined together. In the illustrated example, valve cap 30 includes ring 30A, lock 30B, and half-pipe 30C.

Ring 30A includes one or more circular or ring-like structures. As shown in FIG. 3E, ring 30A may include two ring-shaped structures of different diameters, configured to join (and/or hermetically seal) valve 28 with hub 20. For example, ring 30A may include a larger-diameter ring structure configured to match a diameter of the proximal end of hub 20, and a second, smaller-diameter ring structure configured to match or house a distal end of valve 28.

Lock 30B is a U-shaped or horseshoe-shaped structure extending distally (e.g., in the y-axis direction) from ring 30A. Lock 30B is configured to receive and surround locking bump 42. Locking bump 42 is a protrusion extending radially (e.g., in the x-axis directions) from hub 20. By surrounding locking bump 42, lock 30B may secure hub 20 in place with respect to valve cap 30, for example, preventing separation between the two components in the y-axis direction. In some examples, lock 30B defines a rectangular central opening configured to receive locking bump 42, which may also be generally rectangle-shaped.

Half-pipe 30C is a semi-cylindrical element extending proximally (e.g., in the negative y-axis direction) from ring 30A. Half-pipe 30C is configured to receive and support an underside of clamp tube 60. For example, when clamping assembly 38 is engaged (e.g., in the "locked" position), clamp tube 60 may be compressed between half-pipe 30C on the underside and spade 36 on the top side.

Figure 4C:
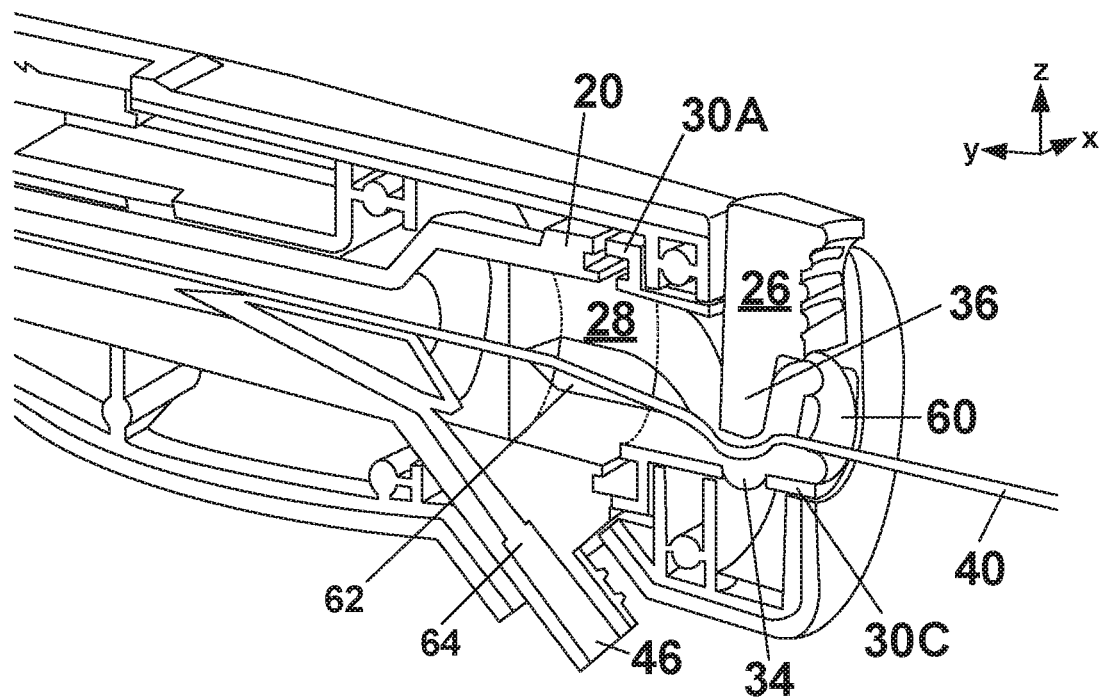
FIG. 4C is a perspective cross-sectional view illustrating the example delivery catheter of FIG. 1.

FIG. 3F further depicts the underside of half-pipe 30C. In some examples, half-pipe 30C defines pinch window 34. Pinch window 34 is an opening, such as a rectangular opening, configured to receive a portion of clamp tube 60 when clamp assembly 38 is in a "locked" position. For example, pinch window 34 may be disposed directly opposite from spade 36, such that spade 36 forces or presses a portion of clamp tube 60 downward (in the negative z-axis) into pinch window 34. As shown in FIGS. 4A-4C, the deformation of clamp tube 60 into pinch window 34 provides a more tortuous path for inner tool 40 through the lumen of clamp tube 60. The more tortuous path may provide more contact area and contact force between inner tool 40 and clamp tube 60, increasing the amount of friction between the elements and securing mechanical tether 40 more firmly in place.

FIGS. 4A-4C are cross-sectional views of handle 14 of the delivery catheter 48 of FIG. 1. Specifically, FIGS. 4A-4C illustrate clamping mechanism 38 of handle 14, configured in a "locked" configuration. In the "locked" configuration, clamp button 26 has been pressed in the negative-z-axis direction, forcing spade 36 downward into the outer surface of clamp tube 60, which may be the proximal end of valve 28. In response, the flexible material of clamp tube 60 compresses or deforms, collapsing or pinching its inner lumen around inner tool 40. A portion of clamp tube 60 deforms into pinch window 34 of half-pipe 30C, further deforming the inner lumen of clamp tube 60. Accordingly, inner tool 40 is forced to bend or curve in the region between spade 36 and pinch window 34. This bending of inner tool 40 further reduces or prevents any proximal or distal motion of inner tool 40 through the inner lumen of clamp tube 60.

Figure 5A:
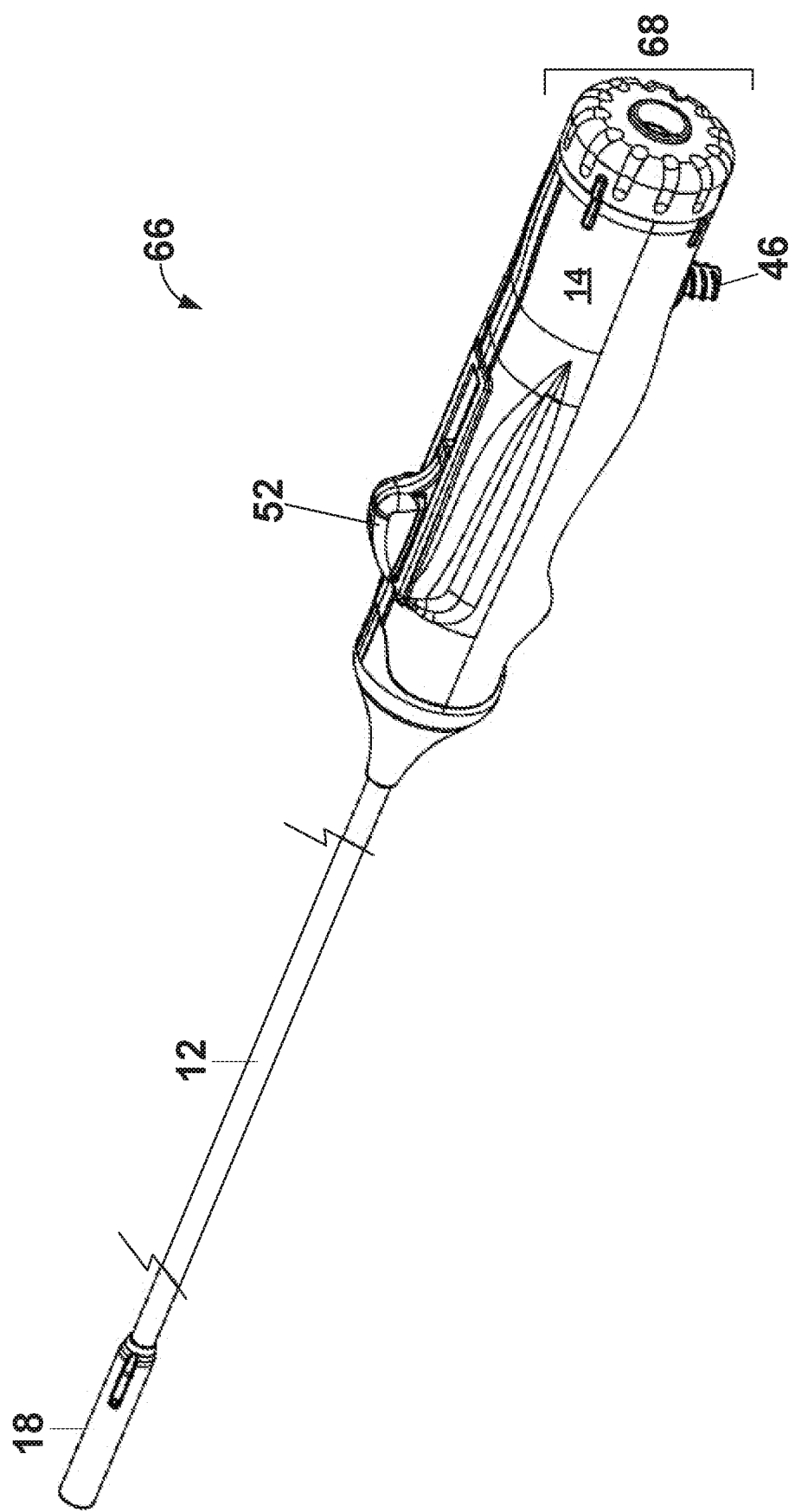
FIG. 5A is a perspective view of another example delivery catheter, in accordance with techniques of this disclosure.
Figure 5B:
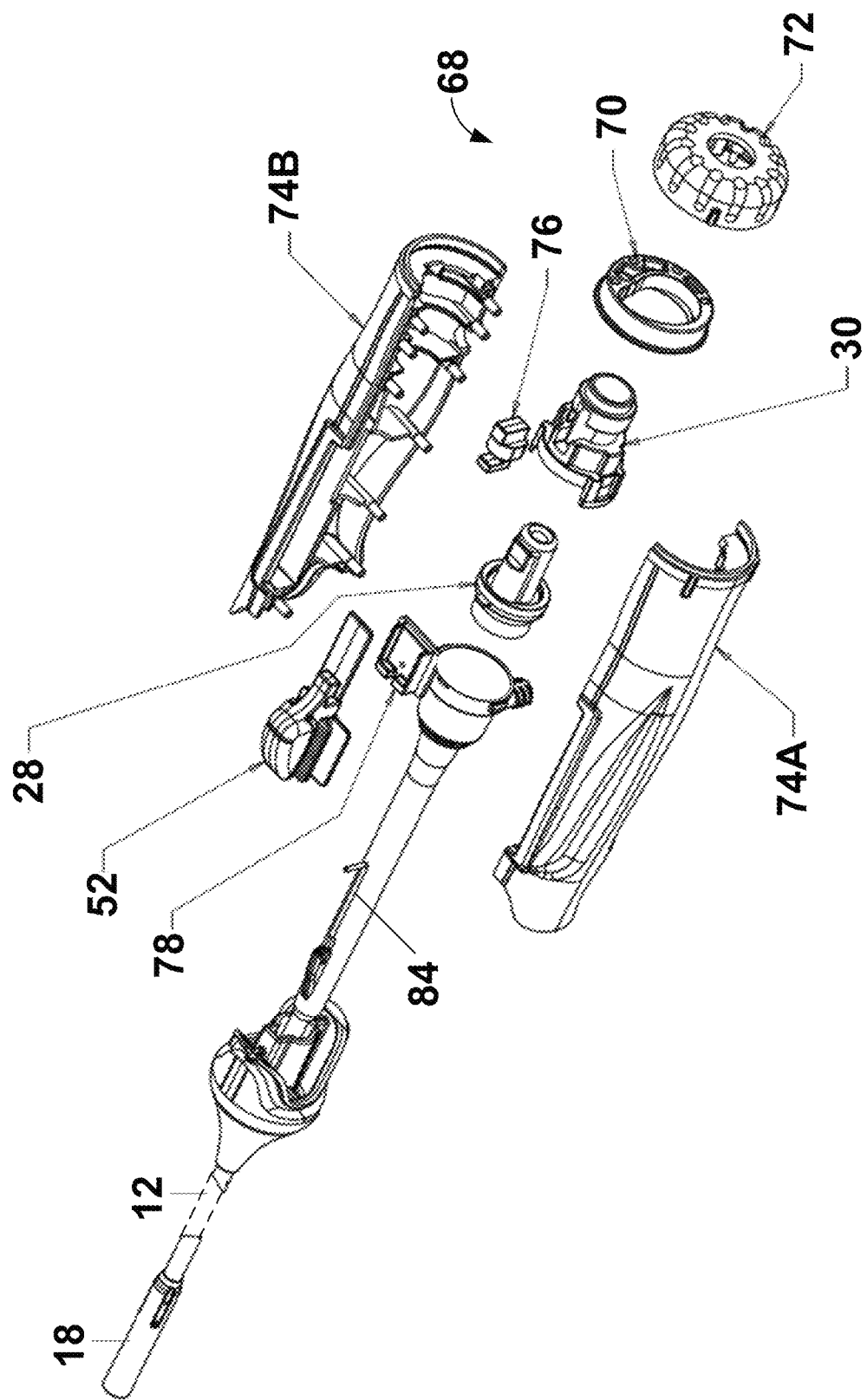
FIG. 5B is an exploded view of the example delivery catheter of FIG. 5A.

FIGS. 5A-5D illustrate another example medical device delivery catheter 66, in accordance with the techniques of this disclosure. Delivery catheter 66 may be an example of inner member or delivery catheter 48 of FIGS. 1-4C. Like numbered elements in FIGS. 5A-5D may be configured and function in a substantially similar manner to that described with respect to FIGS. 1-4C, except as noted herein. FIG. 5A is a perspective view of delivery catheter 66, FIG. 5B is an exploded view of catheter 66, FIG. 5C is a longitudinal cross-sectional side view of catheter 66, and FIG. 5D is a cross-sectional end view of catheter 66 as viewed from axis B-B of FIG. 5C.

As shown in FIG. 5A, delivery catheter 66 includes a handle 14 (e.g., handle 14 of FIGS. 1-4C) having an additional rotary mechanism 68 to assist a user to depress button 76 (FIG. 5B) radially inward into valve 28, so as to clamp valve 28 shut around an inner tool 40 (FIG. 1). As shown in the exploded view of FIG. 5B, rotary mechanism 68 includes inner cam lock ring 70, outer cam lock 72, and button 76. Handle 14 further includes tip button 52, housing portions 74A and 74B and pull block 78. Housing portions 74A and 74B contain the internal components of handle 14, such as valve 28, button 76, and inner cam lock ring 70. Pull block 78 serves to slidably connect tip button 52 to a distal end of catheter 66, such as via pull wire 84.

Figure 6A:
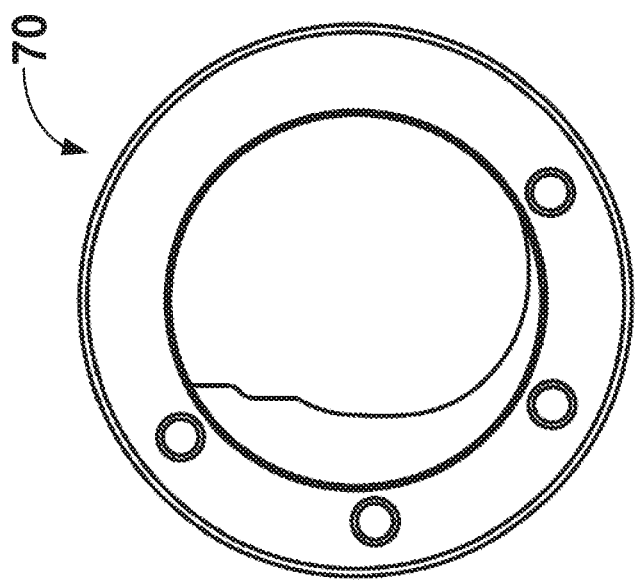
FIGS. 6A and 6B are plan views of an example component of the delivery catheter of FIG. 5A.
Figure 6B:
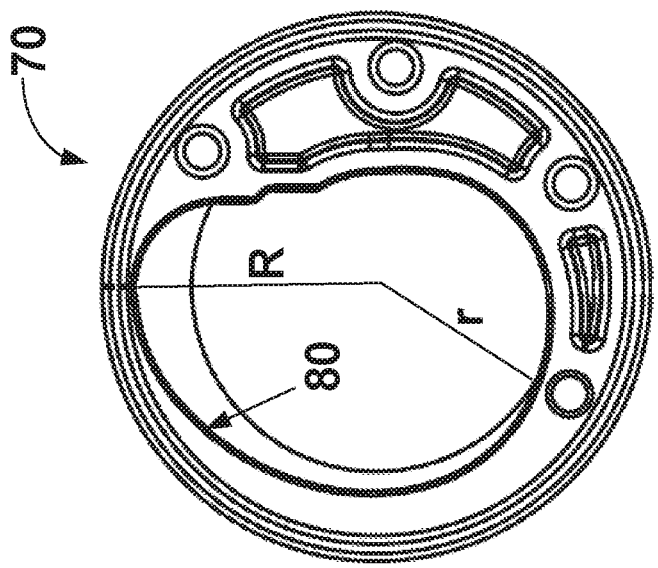

During use, a user such as a physician may apply rotational pressure to rotary mechanism 68, via outer cam lock 72, which is rigidly coupled to inner cam lock ring 70. As shown in greater detail in FIGS. 6A and 6B, inner cam lock ring 70 includes curvilinear inner edge 80 configured to contact button 76. Curvilinear inner edge 80 defines a portion of a spiral pattern, such that the radius of curvature of curvilinear inner edge 80 decreases from first radius "R" to second radius "r" along a counter-clockwise direction, from the perspective shown in FIG. 6A. Accordingly, as the user rotates outer cam lock 72 in a clockwise direction, the portion of inner edge 80 that contacts button 76 decreases in radius of curvature, causing button 76 to depress radially inward toward valve 28, causing valve 28 to collapse around inner tool 40, thereby securing inner tool 40 in place. In order to unlock or release inner tool 40, the physician may apply counter-clockwise rotational pressure to outer cam lock 72 to rotate inner cam lock ring 70, enabling the material of valve 28 to naturally expand back to an expanded configuration.

Figure 7A:
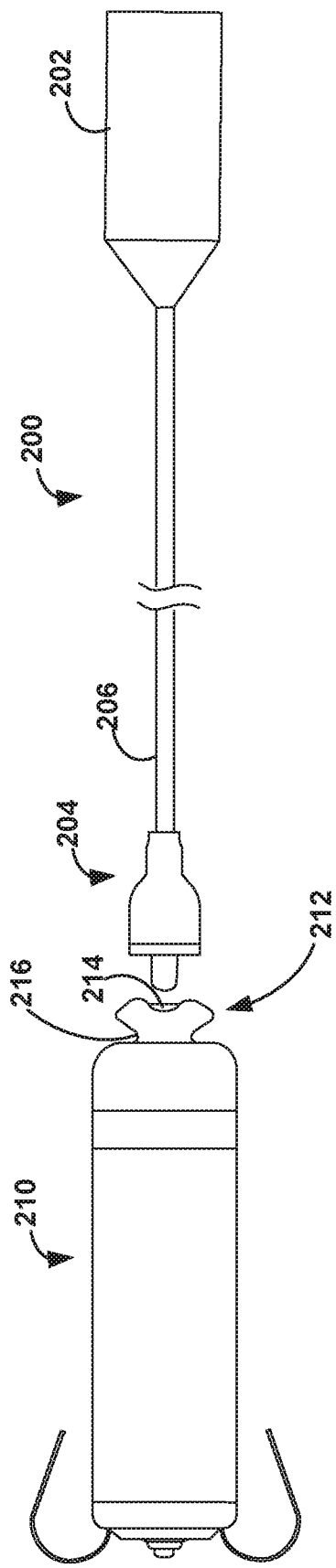
FIGS. 7A and 7B are perspective views illustrating example inner tools that may be utilized with a delivery catheter configured according to the techniques of this disclosure.
Figure 7B:
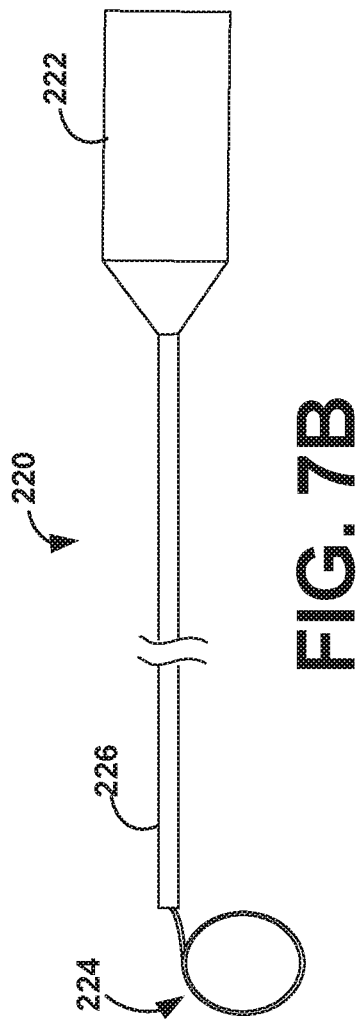

FIGS. 7A and 7B are perspective views illustrating examples of inner tools 40 that may be utilized with a delivery catheter configured according to the techniques of this disclosure. In particular, FIG. 7A illustrates an example configuration of a mechanical tether 200 that may be configured to implant an IMD 210 within a vasculature of a patient. FIG. 7B illustrates an example configuration of a snare 220 that may be configured to retrieve IMD 210 from within a vasculature of a patient. Both mechanical tether 200 and snare 220 may be configured to be received within and slidably extend through the various lumen of delivery catheter 48 described herein, and be engaged by clamping assembly 38 of the delivery catheter, as described herein with respect to inner tool 40 (FIG. 1).

As illustrated in FIG. 7A, mechanical tether 200 may include an elongated shaft 206, a handle 202 at a proximal end of elongated shaft 206, and a tether head assembly 204 at a distal end of elongated shaft 206. Elongated shaft 206 may be of sufficient length that a clinician may manipulate handle 202 to advance tether head assembly 204 out of distal opening of a device cup 18 of delivery catheter 48. Handle 202 may include buttons, sliders, or other actuatable elements to allow a clinician to manipulate mechanical tether 200, e.g., deflect or otherwise steer elongated shaft 206, and/or selectively connect and disconnect tether head assembly 204 from IMD 210.

In the example of FIG. 7A, a proximal end of IMD 210 includes an attachment member 212 comprising an inner attachment element 214 and a neck portion 216. Tether head assembly 204 may have one or more features that are actuatable via handle 202 and configured to selectively receive, retain, grasp, capture, or otherwise connect to attachment member 212, e.g., to inner attachment element 214 or neck portion 216. Example configurations of mechanical tethers and attachment members of IMD, and techniques for using the same, are described in commonly-assigned U.S. Provisional Patent Application No. 62/844,674, filed on May 7, 2019, and incorporated herein by reference in its entirety.

As illustrated in FIG. 7B, snare 220 may include an elongated shaft 226, a handle 222 at a proximal end of elongated shaft 226, and a snare assembly 224 at a distal end of elongated shaft 226. Elongated shaft 226 may be of sufficient length that a clinician may manipulate handle 222 to advance snare assembly 224 out of a distal end of delivery catheter 48. Handle 222 may include buttons, sliders, or other actuatable elements to allow a clinician to manipulate snare 220, e.g., deflect or otherwise steer elongated shaft 226, and/or selectively advance, retract, or steer snare assembly 224 to retrieve IMD 210. Snare assembly 224 may be slidably engaged within elongated shaft 226 to expand (e.g., open) and contract (e.g., close) one or more loop thereof. In some examples, snare assembly 224 may include one or more loops, e.g., metal wire loops. In other examples, snare assembly 224 may additionally or alternatively include one or more nets or stent-like elements configured to expand or contract. In these and other examples, snare assembly 224 may include elements configured to extend over attachment member 212, and then be actuated to a reduced sized configured to capture attachment member 212, e.g., to grasp attachment member at neck portion 216. Example configurations of snares and attachment members of IMD, and techniques for using the same, are described in commonly-assigned U.S. Provisional Patent Application No. 62/743,939, filed on Oct. 10, 2018, and incorporated herein by reference in its entirety.

Figure 8:
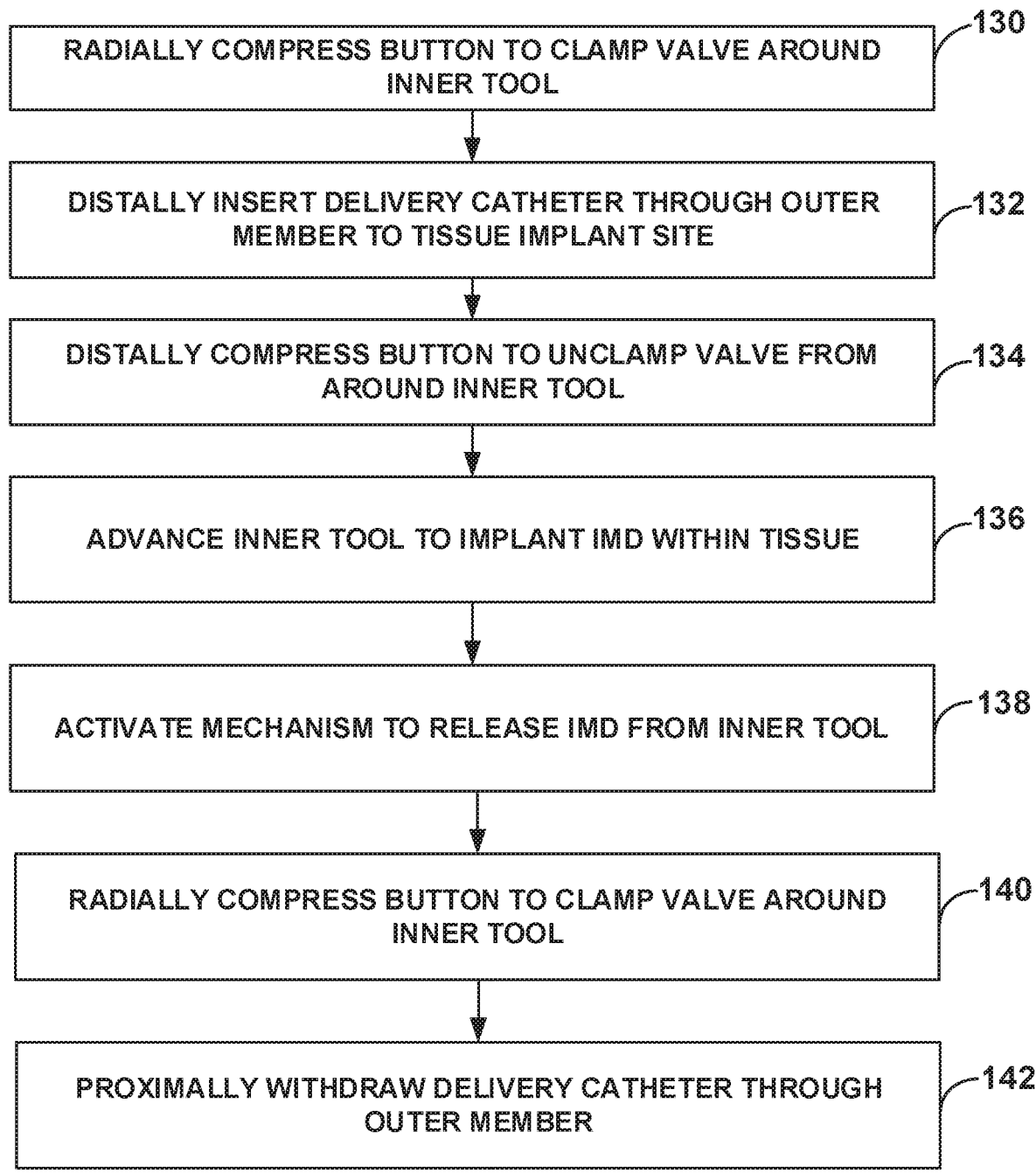
FIG. 8 is a flow diagram illustrating an example method of delivering an IMD within a vasculature of a patient using a delivery catheter configured in accordance with some techniques of this disclosure.

FIG. 8 is a flow chart illustrating a method of delivering an IMD within a vasculature of a patient, in accordance with some techniques of this disclosure. The method of FIG. 5 is described with respect to the system and components of FIG. 1, but may be performed with other similar systems and components. A physician or other qualified user or operator may radially compress clamp button 26 on handle 14 at a proximal end of an IMD delivery catheter 48 to engage clamping assembly 38 (130). Radially compressing clamp button 26 causes a set of button teeth 22 to engage with a set of body teeth 24, retaining clamp button 26 in a locked position. In this locked position, a spade 36 engages with an outer surface of clamp tube 60, deforming clamp tube 60 and collapsing its inner lumen around an elongated inner tool 40 passing through the lumen. Additionally, a portion of the outer surface of clamp tube 60 that is opposite spade 36 may wedge into pinch window 34, further deforming the interior lumen of clamp tube 60 against the inner tool, retaining the inner tool firmly in place. In some examples, inner tool 40 may include an elongated tether configured to deliver IMD to an implant site within the vasculature of a patient. In other examples, inner tool 40 may include a snare configured to retrieve IMD from within the vasculature of a patient.

Once inner tool 40 is locked in place by clamping assembly 38, the physician may distally insert and advance delivery catheter 48 through the lumen of an introducer or outer member 16 toward a tissue implant site within the vasculature of the patient (132). In some examples, the physician may manipulate an element, such as tip button 52 on handle 14, to bend or curve the distal end of delivery catheter 48 to navigate beyond the distal end of introducer 16.

Once the distal end of delivery catheter 48 has approached a tissue implant site, the physician may distally press clamp button 26 to unclamp clamp tube 60 from around inner tool 40 to disengage clamping assembly 38 (134). Distally pressing clamp button 26 causes button teeth 22 to disengage from body teeth 24, and the expansion of clamp tube 60 will force clamp button 26 radially to its original "unlocked" position.

Once inner tool 40 has been unclamped from clamp tube 60, the physician may actuate inner tool 40, e.g., distally advance inner tool 40 out of device cup 18, or otherwise move inner tool 40 through valve lumen 62 and other lumen of delivery catheter 48 described herein, to implant engage one or more fixation members of the IMD into tissue the tissue implant site (136). The physician may then further actuate inner tool 50 by activating a mechanism, such as a button or switch, on the proximal end of inner tool 40 to release the IMD from the distal end of inner tool 40 (138). In some examples, but not all examples, the physician may then radially compress button 26 to once again pinch clamp tube 60 around inner tool 40 (140). Finally, the physician may proximally withdraw delivery catheter 48 through outer member 16 (142).

In some examples, the physician may partially depress button 26 to apply a holding force to tool 40, without completely clamping valve 28 shut. For example, the physician may use the partially depressed button 26 to apply resistance to tool 40 to generally hold it in position, yet still allow tool 40 to be moved if needed by applying more force to the tool. This may enable the physician to implant or retrieve an IMD without requiring an assistant to operate either handle 14 or tool 40. This could be especially useful when utilizing tool 40 as a snare to retrieve the IMD 210.

The following clauses provide some examples of the disclosure.

Clause 1: In some examples, an implantable medical device delivery catheter includes: a shaft configured to extend through a vasculature of a patient, wherein the shaft comprises a shaft lumen extending from a proximal end of the shaft to a distal end of the shaft; and a handle connected to the proximal end of the shaft, the handle comprising: an elongated member disposed within the handle, the elongated member comprising an elongated member lumen in fluid communication with the shaft lumen, wherein the elongated member lumen and the shaft lumen are configured to receive an inner tool configured to extend through the elongated member lumen and the shaft lumen and interface with the implantable medical device; and a clamping assembly including a button configured to be actuated toward a longitudinal axis of the elongated member in a direction transverse to the longitudinal axis to compress the elongated member against the inner tool to restrain movement of the inner tool through the elongated member lumen.

Clause 2: In some examples of the delivery catheter of clause 1, the button is configured to be actuated from a first position to a second position in which the button compresses the elongated member against the inner tool.

Clause 3: In some examples of the delivery catheter of clause 2, the clamping assembly includes a set of distal-facing teeth and the button includes a set of proximal-facing teeth configured to engage with the set of distal-facing teeth and hold the button in the second position.

Clause 4: In some examples of the delivery catheter of clause 2, the button is further configured to be actuated from the second position to the first position in response to a longitudinal force in a direction of the distal end of the catheter.

Clause 5: In some examples of the delivery catheter of any of clauses 2 to 4, the button further includes a spade configured to engage with an outer surface of the elongated member.

Clause 6: In some examples of the delivery catheter of any of clauses 1 to 5, the elongated member includes a flexible polymer.

Clause 7: In some examples of the delivery catheter of clause 6, the flexible polymer comprises rubber.

Clause 8: In some examples of the delivery catheter of any of clauses 1 to 7, the clamping assembly includes a valve cap.

Clause 9: In some examples of the delivery catheter of clause 8, the valve cap includes a semi-cylindrical member configured to support an underside of the elongated member.

Clause 10: In some examples of the delivery catheter of clause 9, the semi-cylindrical member defines a pinch window configured to receive a portion of the elongated member to distort the lumen of the elongated member when the clamping assembly is engaged with the elongated member.

Clause 11: In some examples of the delivery catheter of clause 9 or clause 10, the clamping assembly is configured to compress the elongated member between a button and the semi-cylindrical member, the button configured to be actuated toward a longitudinal axis of the elongate member in a direction transverse to the longitudinal axis of the elongate member.

Clause 12: In some examples of the delivery catheter of clause 8, the valve cap further includes a locking mechanism configured to secure the valve cap to the elongated member.

Clause 13: In some examples of the delivery catheter of any of clauses 1 to 12, the clamping assembly is disposed at a proximal end of the handle.

Clause 14: In some examples, a method includes: engaging a clamping assembly of a handle of a medical device delivery catheter for a first time to restrain movement of an inner tool through an elongated member lumen of an elongated member disposed within the handle, wherein engaging the clamping assembly includes actuating a button of the clamping assembly toward a longitudinal axis of the elongate member in a direction transverse to the longitudinal axis to compress the elongated member against the inner tool; with the clamping assembly engaged for the first time, introducing a distal end of a shaft of the delivery catheter into a vasculature of a patient toward a tissue site, wherein the shaft includes a shaft lumen extending from a proximal end of the shaft to a distal end of the shaft, wherein the handle is connected to the proximal end of the shaft, wherein the shaft lumen is in fluid communication with the elongated member lumen, wherein the shaft lumen and the elongated member lumen are configured to receive the inner tool, and wherein the inner tool is configured to interface with an implantable medical device; releasing the clamping assembly, wherein releasing the clamping assembly includes actuating the button of the clamping assembly away from the longitudinal axis of the elongate member; with the clamping assembly released, actuating the inner tool, wherein actuating the inner tool includes moving the inner tool through the shaft lumen and the elongated member lumen; after actuating the inner tool, engaging the clamping assembly a second time to restrain movement of the inner tool through the elongated member lumen; and with the clamping assembly engaged the second time, proximally withdrawing the shaft from the patient.

Clause 15: In some examples of the method of clause 14, engaging the clamping assembly includes actuating the button from a first position to a second position in which the button compresses the elongated member against the inner tool.

Clause 16: In some examples of the method of clause 15, the clamping assembly locks the button in the second position, and releasing the clamping assembly includes unlocking the clamping assembly.

Clause 17: In some examples of the method of clause 15, engaging the clamping assembly includes manually holding the clamping assembly in the second position.

Clause 18: In some examples of the method of any of clauses 14 to 17, the inner tool is a mechanical tether, and actuating the inner tool includes releasing the implantable medical device from the tether.

Clause 19: In some examples of the method of any of clauses 14 to 17, the inner tool is a snare, and actuating the inner tool includes grabbing the implantable medical device with a distal end of the snare.

Clause 20: In some examples, a system includes the delivery catheter of clause 1 and an inner tool.

Clause 21: In some examples of the system of clause 20, the inner tool includes a mechanical tether configured to implant an IMD within a vasculature of a patient.

Clause 22: In some examples of the system of clause 20, the inner tool includes a snare configured to retrieve an IMD from within a vasculature of a patient.

Clause 23: In some examples of the system of any of clauses 20 to 22, the system further includes the implantable medical device, wherein the implantable medical device includes a pacemaker.

Various aspects of the disclosure have been described. These and other aspects are within the scope of the following claims.

What is claimed is:

1. An implantable medical device delivery catheter comprising:
    a shaft configured to extend through a vasculature of a patient, wherein the shaft comprises a shaft lumen extending from a proximal end of the shaft to a distal end of the shaft; and
    a handle connected to the proximal end of the shaft, the handle comprising:
       an elongated member disposed within the handle, the elongated member comprising an elongated member lumen in fluid communication with the shaft lumen, wherein the elongated member lumen and the shaft lumen are configured to receive an inner tool configured to extend through the elongated member lumen and the shaft lumen and interface with an implantable medical device; and
       a clamping assembly comprising a button configured to be actuated toward a longitudinal axis of the elongated member in a direction transverse to the longitudinal axis to compress the elongated member against the inner tool to restrain movement of the inner tool through the elongated member lumen, wherein the clamping assembly comprises a semi-cylindrical member configured to support an underside of the elongated member, wherein the button is configured to be actuated from a first position to a second position in which the button compresses the elongated member against the inner tool, and wherein the button is further configured to be actuated from the second position to the first position in response to a longitudinal force in a direction of the distal end of the catheter.

2. The delivery catheter of claim 1, wherein the clamping assembly comprises a first set of teeth and the button comprises a second set of teeth configured to engage with the first set of teeth and hold the button in the second position.

3. The delivery catheter of claim 1, wherein the button further comprises a spade configured to engage with an outer surface of the elongated member.

4. The delivery catheter of claim 1, wherein the elongated member comprises a flexible polymer.

5. The delivery catheter of claim 4, wherein the flexible polymer comprises rubber.

6. The delivery catheter of claim 1, wherein the semi-cylindrical member defines a pinch window configured to receive a portion of the elongated member to distort the lumen of the elongated member when the clamping assembly is engaged with the elongated member.

7. The delivery catheter of claim 1, wherein the clamping assembly is configured to compress the elongated member between the button and the semi-cylindrical member.

8. The delivery catheter of claim 1, wherein the clamping assembly comprises a valve cap comprising a locking mechanism configured to secure the valve cap to the elongated member.

9. The delivery catheter of claim 1, wherein the clamping assembly is disposed at a proximal end of the handle.

10. A method comprising:
    engaging a clamping assembly of a handle of a medical device delivery catheter for a first time to restrain movement of an inner tool through an elongated member lumen of an elongated member disposed within the handle, wherein engaging the clamping assembly comprises actuating a button of the clamping assembly toward a longitudinal axis of the elongate member in a direction transverse to the longitudinal axis to compress the elongated member against the inner tool, wherein the clamping assembly comprises a semi-cylindrical member configured to support an underside of the elongated member, wherein engaging the clamping assembly comprises actuating the button from a first position to a second position in which the button compresses the elongated member against the inner tool, and wherein the button is further configured to be actuated from the second position to the first position in response to a longitudinal force in a direction of the distal end of the catheter;
    with the clamping assembly engaged for the first time, introducing a distal end of a shaft of the delivery catheter into a vasculature of a patient toward a tissue site, wherein the shaft comprises a shaft lumen extending from a proximal end of the shaft to a distal end of the shaft, wherein the handle is connected to the proximal end of the shaft, wherein the shaft lumen is in fluid communication with the elongated member lumen, wherein the shaft lumen and the elongated member lumen are configured to receive the inner tool, and wherein the inner tool is configured to interface with an implantable medical device;
    releasing the clamping assembly, wherein releasing the clamping assembly comprises actuating the button of the clamping assembly away from the longitudinal axis of the elongate member;
    with the clamping assembly released, actuating the inner tool, wherein actuating the inner tool comprises moving the inner tool through the shaft lumen and the elongated member lumen;
    after actuating the inner tool, engaging the clamping assembly a second time to restrain movement of the inner tool through the elongated member lumen; and
    with the clamping assembly engaged the second time, proximally withdrawing the shaft from the patient.

11. The method of claim 10, wherein the clamping assembly locks the button in the second position, wherein releasing the clamping assembly comprises unlocking the clamping assembly.

12. The method of claim 10, wherein engaging the clamping assembly comprises manually holding the clamping assembly in the second position.

13. The method of claim 10, wherein the inner tool is a mechanical tether, and wherein actuating the inner tool comprises releasing the implantable medical device from the tether.

14. The method of claim 10, wherein the inner tool is a snare, and wherein actuating the inner tool comprises grabbing the implantable medical device with a distal end of the snare.

15. A system comprising:
    an implantable medical device, wherein the implantable medical device comprises a pacemaker;
    an inner tool; and
    a delivery catheter comprising:
       a shaft configured to extend through a vasculature of a patient, wherein the shaft comprises a shaft lumen extending from a proximal end of the shaft to a distal end of the shaft; and
       a handle connected to the proximal end of the shaft, the handle comprising:

an elongated member disposed within the handle, the elongated member comprising an elongated member lumen in fluid communication with the shaft lumen, wherein the elongated member lumen and the shaft lumen are configured to receive the inner tool configured to extend through the elongated member lumen and the shaft lumen and interface with the implantable medical device; and a clamping assembly comprising a button configured to be actuated toward a longitudinal axis of the elongated member in a direction transverse to the longitudinal axis to compress the elongated member against the inner tool to restrain movement of the inner tool through the elongated member lumen, wherein the clamping assembly comprises a semi-cylindrical member configured to support an underside of the elongated member.

16. The system of claim 15, wherein the inner tool comprises a mechanical tether configured to implant an implantable medical device within a vasculature of a patient.

17. The system of claim 15, wherein the inner tool comprises a snare configured to retrieve an implantable medical device from within a vasculature of a patient.

18. An implantable medical device delivery catheter comprising:
   a shaft configured to extend through a vasculature of a patient, wherein the shaft comprises a shaft lumen extending from a proximal end of the shaft to a distal end of the shaft; and
   a handle connected to the proximal end of the shaft, the handle comprising:
      an elongated member disposed within the handle, the elongated member comprising an elongated member lumen in fluid communication with the shaft lumen, wherein the elongated member lumen and the shaft lumen are configured to receive an inner tool configured to extend through the elongated member lumen and the shaft lumen and interface with an implantable medical device; and
      a clamping assembly comprising a button configured to be actuated toward a longitudinal axis of the elongated member in a direction transverse to the longitudinal axis to compress the elongated member against the inner tool to restrain movement of the inner tool through the elongated member lumen, wherein the button is configured to be actuated from a first position to a second position in which the button compresses the elongated member against the inner tool, wherein the button is further configured to be actuated from the second position to the first position in response to a longitudinal force in a direction of the distal end of the catheter, wherein the clamping assembly comprises a first set of teeth facing a first direction and the button comprises a second set of teeth facing a second direction, and wherein the second set of teeth is configured to engage with the first set of teeth and hold the button in the second position.

19. The delivery catheter of claim 18, wherein the button further comprises a spade configured to engage with an outer surface of the elongated member.

20. The delivery catheter of claim 18, wherein the elongated member comprises a flexible polymer.

21. The delivery catheter of claim 20, wherein the flexible polymer comprises rubber.

22. The delivery catheter of claim 18, wherein the clamping assembly comprises a semi-cylindrical member that defines a pinch window configured to receive a portion of the elongated member to distort the lumen of the elongated member when the clamping assembly is engaged with the elongated member.

23. The delivery catheter of claim 18, wherein the clamping assembly comprises a semi-cylindrical member configured to support an underside of the elongated member, and wherein the clamping assembly is configured to compress the elongated member between the button and the semi-cylindrical member.

* * * * *